United States Patent
Wolf

(10) Patent No.: US 9,829,313 B2
(45) Date of Patent: Nov. 28, 2017

(54) SYSTEMS AND METHODS FOR IMPROVED ACCURACY IN DETERMINING ALTITUDE FROM PRESSURE

(71) Applicant: NextNav, LLC, Sunnyvale, CA (US)

(72) Inventor: Thomas Wolf, Mountain View, CA (US)

(73) Assignee: NextNav, LLC, Sunnyvale, CA (US)

(*) Notice: Subject to any disclaimer, the term of this patent is extended or adjusted under 35 U.S.C. 154(b) by 388 days.

(21) Appl. No.: 14/618,137

(22) Filed: Feb. 10, 2015

(65) Prior Publication Data
US 2015/0233713 A1 Aug. 20, 2015

Related U.S. Application Data

(60) Provisional application No. 61/939,814, filed on Feb. 14, 2014.

(51) Int. Cl.
*G01C 5/06* (2006.01)
*G01N 19/10* (2006.01)
*G01K 13/00* (2006.01)

(52) U.S. Cl.
CPC .............. *G01C 5/06* (2013.01); *G01K 13/00* (2013.01); *G01N 19/10* (2013.01)

(58) Field of Classification Search
CPC .......... G01C 5/06; G01K 13/00; G01N 19/10
See application file for complete search history.

(56) References Cited

U.S. PATENT DOCUMENTS

2014/0039823 A1    2/2014  Raghupathy et al.

FOREIGN PATENT DOCUMENTS

| CN | 201528388 U    | 7/2010  |
| CN | 103383462 A    | 11/2013 |
| RU | 2029238 C1     | 2/1995  |
| WO | 2012/088833 A1 | 7/2012  |

OTHER PUBLICATIONS

Form PCT/ISA/220, PCT/US2015/015142, "Notification of Transmittal of the International Search Report and the Written Opinion of the International Searching Authority, or the Declaration", 1 page; Form PCT/ISA/210, PCT/US2015/015142, "International Searching Report", 4 pages; Form PCT/ISA/237, PCT/US2015/015142, "Written Opinion of the International Searching Authority", 7 pages. dated May 8, 2015.

*Primary Examiner* — Kyoung Lee

(57) ABSTRACT

Described are methods, systems, means and machine-readable media embodying program instructions for considering water molecules and other mixtures in air when estimating an altitude of a pressure sensor. In at least one implementation, a measurement of humidity is used to compute a gas constant value, and the computed gas constant value is used to estimate an altitude of a pressure sensor. In another embodiment, the measurement of humidity is compared to a threshold condition related to humidity. Depending on the results of the comparison, the measurement of humidity is used to determine the altitude of the pressure sensor.

33 Claims, 5 Drawing Sheets

| Temperature (K) | Error at 100% humidity and 200m height (Pa) | Maximum Height for Error below 12Pa at 100% Humidity (m) | Maximum Humidity for Error below 12Pa at 200m height (%) |
|---|---|---|---|
| 263 | 2.7 | >500 | >100 |
| 273 | 5.6 | 431 | >100 |
| 283 | 11 | 219 | >100 |
| 293 | 20.2 | 118 | 60 |
| 303 | 35.4 | 67 | 30 |
| 313 | 59.7 | 39 | 20 |

SYSTEMS AND METHODS FOR IMPROVED ACCURACY IN DETERMINING ALTITUDE FROM PRESSURE

FIELD

This disclosure relates generally to positioning systems. More specifically, but not exclusively, the disclosure relates to systems and methods for estimating an altitude of a mobile device using measurements of pressure, temperature and humidity.

BACKGROUND

Determining where an object is located in an urban environment can be quite challenging, particularly where the object is located in a multi-story building. Imprecise estimates of a person's altitude, for example, can delay emergency response times, forcing emergency response units to search several floors instead of one floor. Identifying the wrong floor level at which a person resides can also disrupt efforts to restrict, grant or track that person's access to rooms or information based on the location of that person. Of course, there are many other reasons why an accurate estimate of the location of a person or other object at different altitudes is desirable.

Various approaches have been used to estimate the altitude at which an object resides. For example, one common technique uses estimated distances between the object and various transmitters at known locations, where the estimated distances are determined by means of positioning signals sent from those transmitters to the object. Such transmitters may include orbiting satellites of a Global Navigation Satellite System (GNSS) like the Global Positioning System (GPS), or the transmitters include beacons in a terrestrial network of beacons that are dispersed throughout the urban environment.

Positioning signals from beacons in a terrestrial network are usually adequate for estimating the altitude of an object so long as the object has an unobstructed view of the terrestrial beacons and so long as the beacons are installed at different altitudes. Unfortunately, positioning signals from terrestrial beacons are frequently obstructed by buildings that stand between the beacons and the object. The presence of obstructions like buildings leads to unreliable estimates of the distances between the beacons and the object, which decreases the accuracy of the object's estimated altitude when using those unreliable estimated distances.

Other approaches for estimating the altitude of an object use environmental conditions like pressure and temperature. For example, in co-assigned U.S. application Ser. No. 13/296,067, Wide Area Positioning Systems (Nov. 14, 2011), pressure and temperature information collected at one or more reference locations in an urban environment may be used along with pressure collected by the object to determine an altitude of the object. In dense urban settings with buildings that obstruct positioning signals from beacons, use of environmental conditions like pressure and temperature can provide more-accurate estimates of altitude than using positioning signals. Under some conditions, like humid conditions experienced in many densely populated cities throughout the world, the presence of humidity can decrease the accuracy of an estimated altitude that was computed using pressure and temperature without compensating for the effect that humidity has on pressure. Thus, new and improved approaches that use pressure and temperature to estimate the altitude of an object while compensating for the effect humidity has on pressure are needed.

SUMMARY

Various embodiments, but not necessarily all embodiments, described in this disclosure relate generally to methods, systems (e.g., networks, devices or components), means, and machine-readable media for estimating an altitude of a local pressure sensor residing at a first location. Such systems, methods, means and machine-readable media may compute an estimated altitude of the local pressure sensor by using a measurement of pressure from the local pressure sensor, a measurement of pressure from a remote pressure sensor residing at a second location, a known altitude of the remote pressure sensor, a measurement of temperature from a temperature sensor at the second location or a third location, and a measurement of humidity from a humidity sensor.

DRAWINGS

DESCRIPTION

The present disclosure describes various approaches that consider the effects of airborne water vapor (generally referred to as humidity) on accurately estimating an altitude of an object. Details specifying how humidity is considered are provided after the following overview section, which describes a typical environment within which various aspects of this disclosure operate.

Overview of Systems

Figure 1:
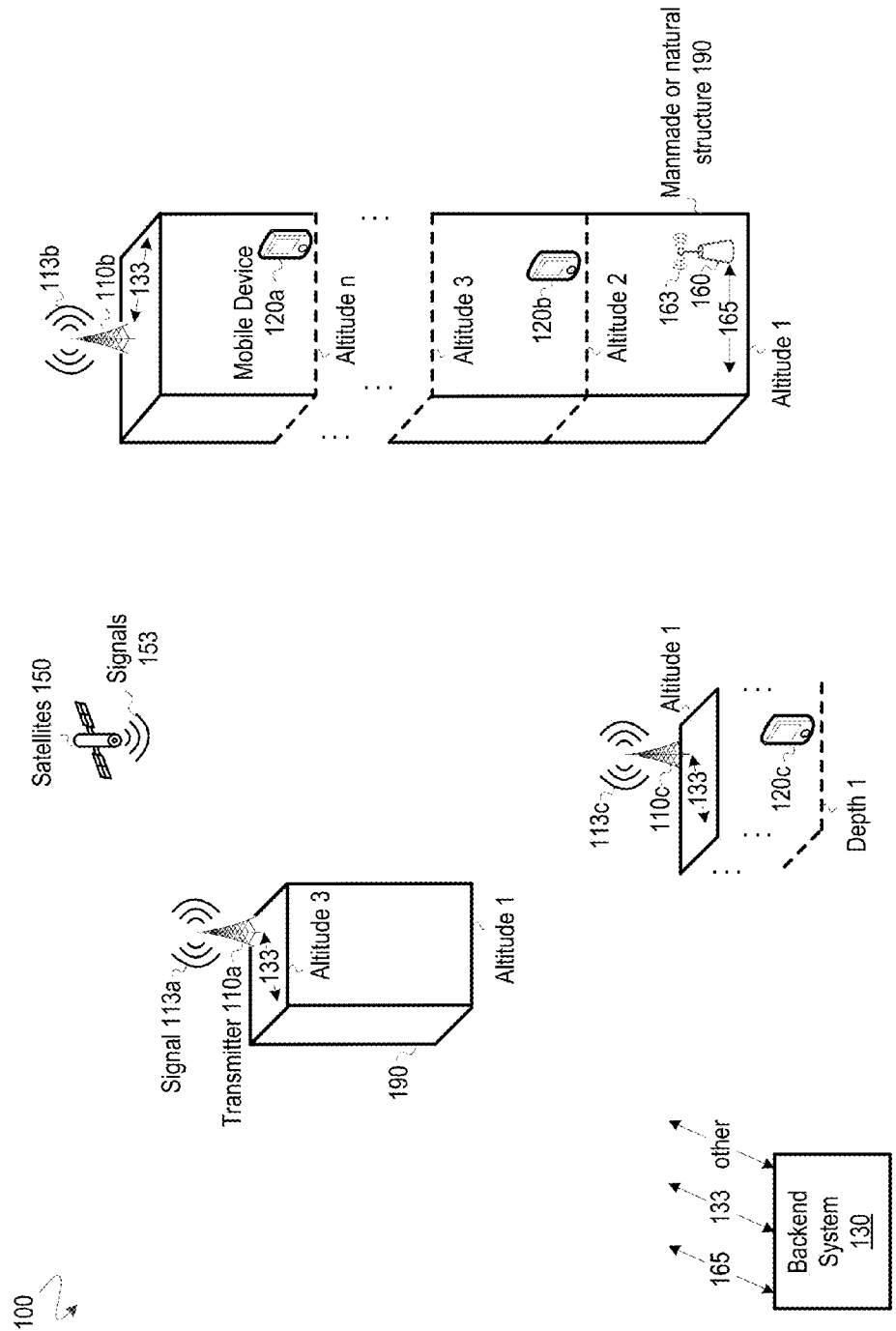
FIG. 1 depicts a positioning system in accordance with one or more embodiments.

FIG. 1 illustrates a positioning system (100) in which various embodiments may be implemented. The system (100) includes any number of mobile device systems ("mobile devices") (120) that receive signals from and/or send signals to transmitter systems ("transmitters") (110), satellite systems ("satellites") (150), and/or other systems ("nodes") (160) via corresponding communication links (113), (153) and (163), respectively. The mobile devices (120) may also receive signals from and/or send signals to other mobile devices (120) and a backend system ("backend") (130) (connectivity not shown).

The transmitters (110) may be configured to transmit signals (113) that are received by any of the mobile devices (120), and to communicate with the backend (130) via the communication links (133). Each signal (113) from each transmitter may carry different information that, once extracted by the mobile device (120) or the backend (130), may identify the following: the transmitter that transmitted the signal; the latitude, longitude and altitude (LLA) of that transmitter; pressure, temperature and other atmospheric conditions at or near that transmitter; ranging information that is used to measure a distance to that transmitter; and other information.

Various mobile devices (120) are depicted at various altitudes above a reference level or depths below the reference level. The mobile devices (120) can be inside or outside various manmade or natural structures (190). Each mobile device (120) may include a location computation engine (not shown) to determine positioning information based on the signals (113) received from the transmitters (110), and/or signals (153) received from the satellites (150), and/or signals (163) received from the nodes (160). The mobile device (120) may include a signal processing component (not shown) that: demodulates the received signals; estimates positioning information like travel time of the received signals and uses the positioning information to estimate the position of the mobile device (120) using trilateration or other processes; and extracts atmospheric information like pressure, temperature and humidity from the received signals to estimate an altitude of the mobile device (120) using that atmospheric information.

The backend (130) communicates with various other systems, such as the transmitters (110), the mobile devices (120), and the other networks (160). The backend system (130) may include one or more processor(s), data source(s), and other components (not shown).

One of ordinary skill in the art will appreciate that methods described herein may be carried out using any or all of the transmitters (110), the mobile devices (120), the backend (130), and other components of the system (100).

Example Transmitter Systems

Figure 2:
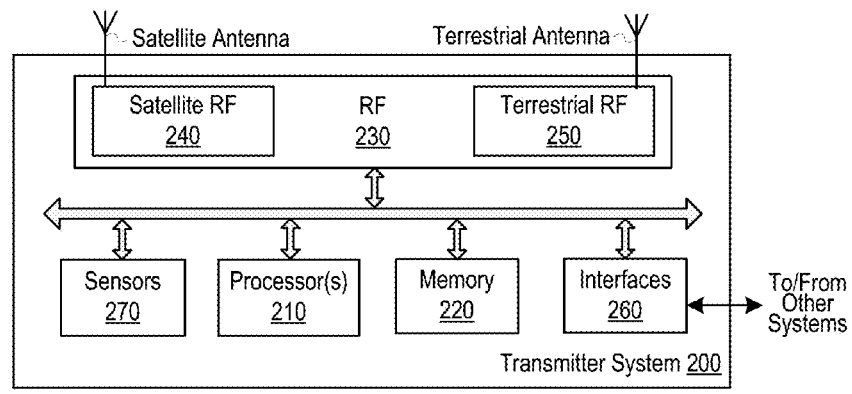
FIG. 2 depicts a transmitter system in accordance with one or more embodiments.

FIG. 2 illustrates details of a transmitter system ("transmitter") (200) at which signals may be generated and transmitted. The transmitter (200) may include a processor (210) that carries out signal processing (e.g., interpreting received signals and generating signals for transmission to other systems). Memory (220) may provide storage and retrieval of data and/or executable instructions for performing methodologies described herein. The transmitter (200) includes satellite and a terrestrial antenna(s) for transmitting and receiving signals, and also includes RF components (230) along with a satellite RF component (240) for receiving satellite signals and a terrestrial RF component (250) for generating and sending output signals to other systems like the mobile devices (120). Generation and reception of signals may be carried out using analog/digital logic and power circuitry, signal processing circuitry, tuning circuitry, buffer and power amplifiers, and other components known by one of ordinary skill in the art. The transmitter (200) may also include an interface (260) for exchanging information with other systems.

Of particular interest to the present disclosure, the transmitter (200) includes one or more environmental sensors (270) for sensing environmental conditions (e.g., pressure, temperature, humidity, wind, sound, or other), which may be used to estimate a position of a mobile device. As will be later described, information specifying the sensed environmental conditions may be transmitted to a mobile device for use in computing the position of the mobile device.

Example Mobile Device Systems

Figure 3:
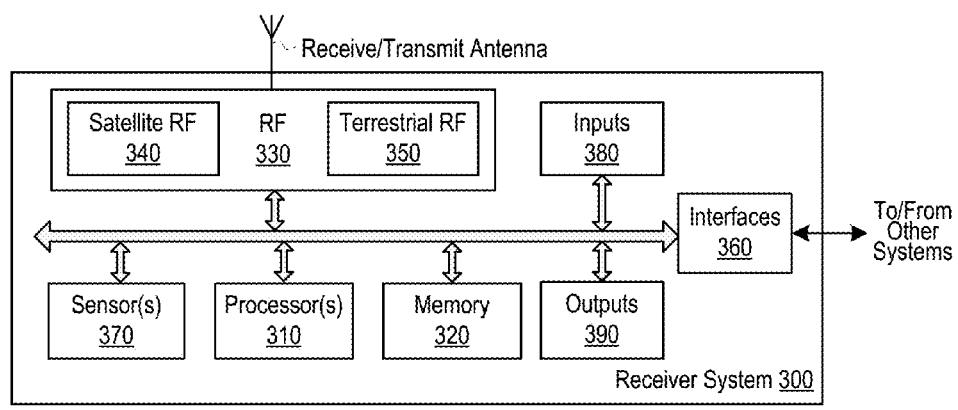
FIG. 3 depicts a mobile device system in accordance with one or more embodiments.

FIG. 3 illustrates details of a mobile device system ("mobile device") (300), at which signals from transmitter systems (e.g., the transmitters (110), satellites (150), and nodes (160) in FIG. 1) may be received and processed to extract information used to compute an estimated position of the mobile device (300). FIG. 3 shows a RF component (330) that facilitates the exchange of information with RF systems. Signal processing occurs at a satellite RF component (340) (e.g., a GPS chip), a terrestrial RF component (350), or other suitable components, which use separate or shared resources such as antennas, RF circuitry, mixers, filters, amplifiers, digital-to-analog and analog-to-digital converters, processors and the like to perform signal processing as is known in the art or otherwise disclosed herein. Of course, other means for exchanging information with other systems is possible, including any wireless or wired transmission over any network via the interface (360). Memory (320) is coupled to a processor (310) to provide storage and retrieval of data and/or instructions relating to methodologies described herein that may be executed by the processor (310). The processor (310) may form all or part of a positioning engine that determines positioning information from signaling received from other systems. The mobile device (300) also includes input and output (I/O) components (380, 390), which may include a keypad, touchscreen display, camera, microphone, speaker, or other components that permit a user to interact with the mobile device (300).

Of particular interest to the present disclosure, the mobile device (300) may include one or more sensors (370) for measuring inertial conditions (e.g., acceleration, velocity, orientation) as well as environmental conditions like pressure, temperature, humidity, wind force, wind direction, light, sound, or other conditions at or near the location of the mobile device (300). By way of example, pressure and temperature information may be used by the processor (310) to determine position information like altitude, which can advantageously allow estimation of the position of a mobile device (120) within a building at floor-level accuracy. Examples of such calculations are illustrated in co-assigned U.S. application Ser. No. 13/296,067, Wide Area Positioning Systems (Nov. 14, 2011).

As described in further detail below, considering humidity improves approaches that use measurements of pressure and temperature to estimate the altitude of the mobile device (300).

Effects of Humidity on Estimates of Altitude

As discussed below, an altitude of a local pressure sensor can be estimated where the altitude of a remote pressure sensor and pressure measurements from both pressure sensors are known. For example, one formulation for the relationship between local altitude h, local atmospheric pressure P, and remote pressure $P_0$ (assumed to be at a sea-level height of 0) is:

$$P_0 = P \exp\left(\frac{hg}{RT}\right), \text{ or } h = \frac{RT}{g} \ln\left(\frac{P_0}{P}\right),$$

where T is a temperature of an environment (e.g., outdoor or indoor), g is acceleration due to gravity, and R is a gas constant specific to dry air. The gas constant R is given by:

$$R = \frac{R_u}{M},$$

where $R_u$=8.31447 J/(mol-K) is the universal gas constant and M is the molar mass of the gas (mass of one mole of the gas). For standard "dry" air comprising mostly nitrogen with some oxygen and negligible amounts of water and other molecules, $M=M_d$=0.0289644 kg/mol, so R is generalized to 287.058 J/(kg-K) for standard dry air. However, not all air is dry, and air that contains water molecules (i.e., air with humidity) has a different molar mass than dry air because water molecules have different mass than oxygen and nitrogen in dry air. For example, the molar mass for pure water vapor, $M_v$, is 0.01816 kg/mol. Thus, for non-standard air (i.e., air with humidity), M for humid air will vary between $M_d$ and $M_v$ depending on the amount of humidity in the air.

When attempting to compute relative altitude between two air pressure sensors, the difference between assuming an R value for standard dry air to compute the relative altitude, and using a computed R value for humid air that accounts for water vapor to determine the relative altitude, can be significant. In some cases, an error of six meters or more can result, which equates to several floor levels in a building. In indoor environments like high-rise buildings in cities, where meter-level accuracy is needed to discern between consecutive floors, failure to account for humidity in the altitude calculation can result in significant errors that result in inaccurate estimates of position that identify a wrong floor. Thus, under certain circumstances, a measurement of humidity in the air can be evaluated, and a computed value of R based on molar mass that accounts for water vapor content in the air can be used to estimate the relative altitude instead of R for standard dry air.

Using Humidity to Compute a Gas Constant for Use in Estimating Relative Altitude Since air pressure is a function of a gas constant R, a temperature T, and an altitude h, conditions of high humidity require unique computations of a gas constant that reflect current humidity levels, and that can be adjusted as humidity rises or falls. Computing a unique gas constant under unique ambient conditions may be accomplished using the following multi-step process.

In a first step, the water vapor saturation pressure, $p_{ws}$, may be determined at the particular temperature of an outdoor environment, which is preferably an outdoor air temperature when sensors are dispersed in outdoor locations. However, an indoor temperature may be used where sensors are dispersed indoors. The temperature may be measured by a suitable sensor of a mobile device and/or a suitable reference sensor, which are remotely located from each other. In some embodiments, such as where the mobile device is located inside a climate-controlled building, the temperature measurement may be measured by a remotely-located reference sensor that is located outside of that building. Of course, multiple measurements from multiple locations may be used to determine a final measurement, where the final measurement is based on an average, weighted average, or other combination of measurements at different locations. A measurement from a weather station may also be suitable depending on the proximity of the weather station to the mobile device.

By way of example, the following empirical relationship specifies a polynomial approximation of water vapor saturation pressure as:

$$p_{ws}=100(a_0+a_1t+a_2t^2+a_3t^3+a_4t^4+a_5t^5+a_6t^6),$$

where t is temperature in centigrade, T is temperature in Kelvin, such that t=T−273.15, and the coefficients are:
  $a_0$=6.107799961
  $a_1$=4.436518521×10⁻¹
  $a_2$=1.428945805×10⁻²
  $a_3$=2.650648471×10⁻⁴
  $a_4$=3.031240396×10⁻⁶
  $a_5$=2.034080948×10⁻⁸
  $a_6$=6.136820929×10⁻¹¹

In a second step, a relative humidity may be measured by a suitable sensor at a mobile device and/or a suitable reference sensor, which are remotely located from each other. As with temperature, where the mobile device is located inside a climate-controlled building, the humidity measurement may be measured by a reference sensor located outside of that building, and, of course, multiple measurements from multiple locations may be used to determine a final measurement. A Humidity Ratio, x, may be found based upon the measured relative humidity, ϕ, the measured air pressure, $p_a$, and the water vapor saturation pressure $p_{ws}$, where $$x=0.62198\phi p_{ws}/(p_a-\phi p_{ws}).$$

In a third step, the gas constant for humid air, $R_m$, may be determined using the gas constant for dry air of $R_{da}$=287.053, where:

$$R_m=R_{da}(1+1.609x)/(1+x).$$

The gas constant for humid air, $R_m$, may then be used for R in the formula relating pressure and altitude.

The significance of using an appropriate gas constant that is based on humidity is illustrated below in relation to FIG. 4 through FIG. 7.

Significance of Humidity and Temperature on Pressure Measurements

The difference between using dry air formulations to compute the relative altitude between two air pressure sensors and using "humid" air formulations can be many meters, where 1 meter of vertical error corresponds to a pressure difference of approximately 12 Pa. For floor-level accuracy, a maximum error of 1 meter (or approximately 12 Pa) is often desired, so minimizing error caused by humidity is important under certain environment conditions.

Figure 4:
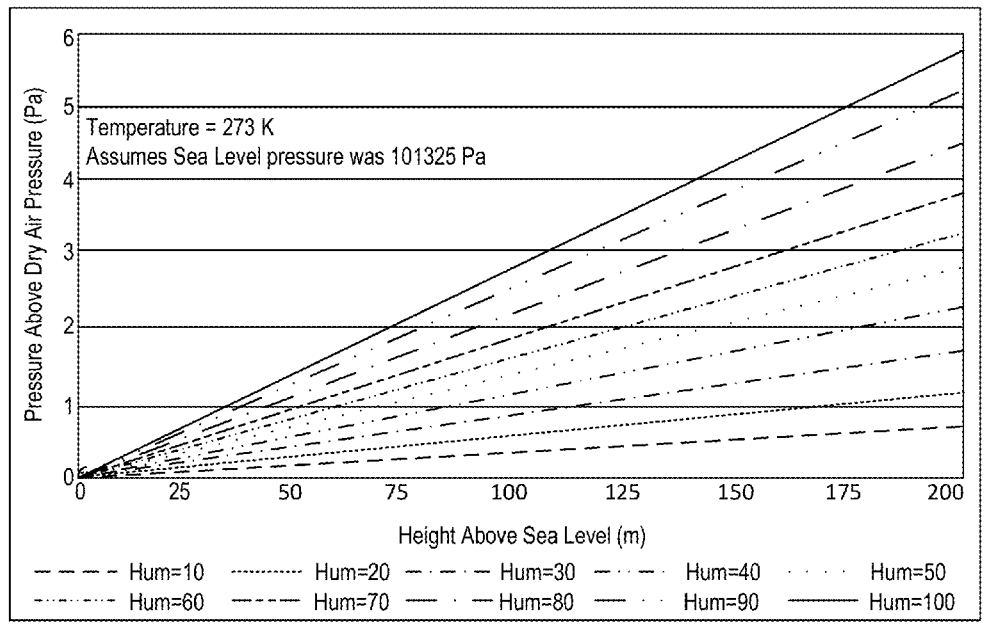
FIG. 4 depicts a graph showing how humidity affects pressure measurements corresponding to different altitudes at a first temperature.
Figure 5:
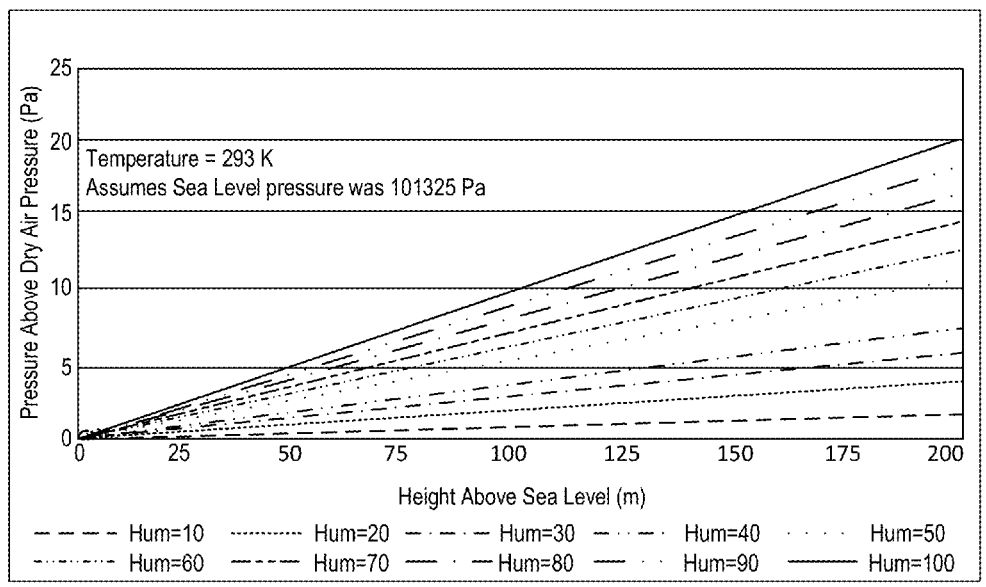
FIG. 5 depicts a graph showing how humidity affects pressure measurements corresponding to different altitudes at a second temperature.
Figures 6, 7:
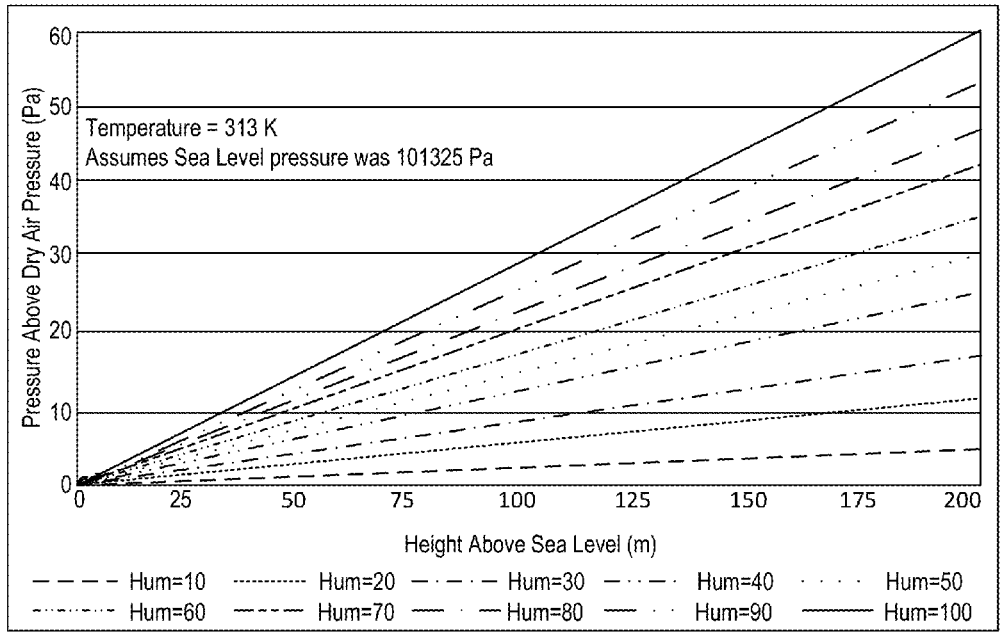
FIG. 6 depicts a graph showing how humidity affects pressure measurements corresponding to different altitudes at a third temperature.
FIG. 7 depicts a table showing how humidity and temperature affect pressure measurements.

By way of illustration, FIG. 4 through FIG. 6 each depicts a graph that compares computations of pressure using a "dry" air formula and using a humid air formula at different altitudes. For each graph, the computations are performed assuming a different air temperature. Each graph specifies a range of different altitudes along the horizontal axis. The vertical axis specifies a difference in measured pressures between computing the pressure using the "dry" air formula and computing the pressure using the "humid" air formula. For each level of humidity ("Hum=[level]"), each graph charts differences between computing the pressure using the "humid" air formula and computing the pressure using the "dry" air formula at different altitudes (also referred to as "heights"). As shown by each graph, higher levels of humidity can result in bigger differences for computed pressure as compared to lower levels of humidity.

The graphs in FIG. 4 through FIG. 6 collectively show that differences in computed pressure corresponding to higher temperatures are larger than differences in computed pressure corresponding to lower temperatures. The graphs in FIG. 4 through FIG. 6 also illustrate that the difference between computed pressure using the "dry" air formula and computed pressure using the "humid" air formula becomes more significant as the altitude difference between two sensors (as designated by any of the altitudes in the horizontal axis) increases when humidity is present.

FIG. 7 depicts a table 700 showing how humidity and temperature affect estimations of altitude, where pressure measurements are used to estimate the altitudes. The table 700 illustrates that different combinations of humidity and temperature become significant depending on the maximum possible altitude between a reference pressure sensor and a pressure sensor of interest (e.g., a pressure sensor of a mobile device).

The first column of the table 700 identifies different levels of temperature.

The second column identifies differences in computed pressures using the "dry" air formula and the "humid" air formula at an altitude of 200 meters, and during 100% humidity. The differences in computed pressures are identified for different temperatures. As shown, a difference above 12 Pa occurs above a threshold temperature that is closer to a temperature of 283 K than a temperature of 293 K. Thus, under conditions of 100% humidity, an ambient temperature that is greater than the threshold temperature may require consideration of humidity when the possible altitude separating the two pressure sensors is at least 200 meters.

The third column of the table 700 identifies maximum altitude differences between the two pressure sensors, below which differences in computed pressures are below 12 Pa for each temperature assuming 100% humidity. As shown, a pressure difference below 12 Pa is possible if the difference in altitude between pressure sensors is less than a threshold altitude that depends on the temperature and the humidity level.

The fourth column of the table 700 identifies threshold levels of humidity at which differences in computed pressure are below 12 Pa for each temperature assuming a maximum altitude difference between pressure sensors of 200 meters. As shown, a difference in computed pressure below 12 Pa is only possible under certain threshold levels of humidity once the temperature exceeds a maximum threshold temperature.

FIG. 4 through FIG. 7 illustrate that humidity should be taken into consideration for meter-level accuracy when estimating an altitude. For example, when an ambient humidity level has reached a threshold level of humidity, or when a combination of an ambient humidity level and an ambient temperature reach threshold levels, data corresponding to the ambient humidity level may be used during estimation of a pressure sensor's altitude.

In certain embodiments, consideration of thresholds is not needed, and humidity is always used to estimate an altitude of a particular pressure sensor. However, in other embodiments, where computations are performed at a mobile device at which the particular pressure sensor resides, a transmitter may consider the thresholds to determine whether to transmit humidity data measured at a reference location. Not sending the humidity data may reduce load on communication channels (e.g., RF channels) between the transmitter and the mobile device. Not sending the humidity data may also reduce processing load associated with processing signals the mobile device receives.

Consideration of the thresholds may also control when results from an altitude computation using a "dry" air formula should be adjusted by predefined amounts given a present level of humidity. For example, when a threshold condition is met, error bounds on a "dry" air calculation may be estimated. In another embodiment, when an accurate measurement of humidity is not available for a particular region within which the pressure sensors reside, another measurement of humidity for a neighboring region may be compared against a threshold condition, and then used to compute the altitude. An adjustment to that humidity, or to the computed altitude, may be made based on an expected difference in humidity corresponding to the two regions (e.g., using historical data).

Examples of Approaches that Consider Humidity when Estimating an Altitude

Various approaches that consider humidity when estimating an altitude of a pressure sensor are described below in relation to FIG. 8, which depicts a method for determining when to estimate an altitude of a pressure sensor using a measurement of humidity.

Figure 8:
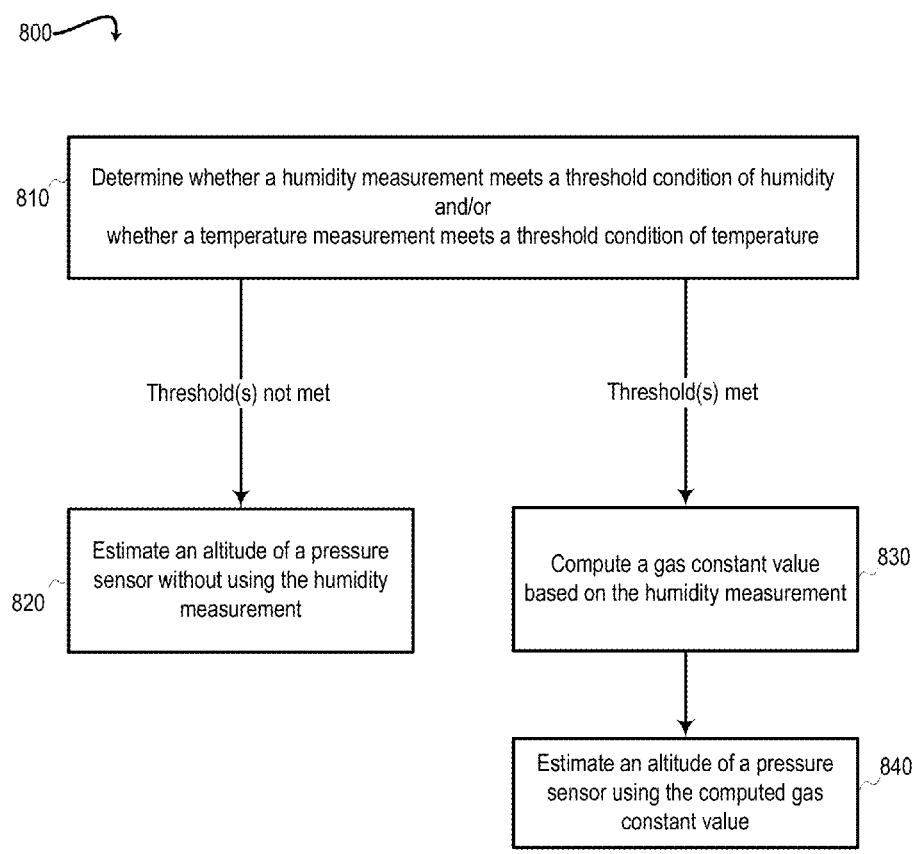
FIG. 8 illustrates a process for determining an altitude of a pressure sensor using a measurement of humidity in accordance with one or more embodiments.

As shown in FIG. 8, a measurement of temperature and/or a measurement of humidity are compared to one or more threshold conditions (810). Accordingly to FIG. 8, if the one or more threshold conditions are not met, then the altitude of the pressure sensor may be estimated without using the measurement of humidity (e.g., using a predefined gas constant value for a standard air like dry air) (820). Alternatively, if the one or more threshold conditions are met, then a computed gas constant value may be determined based on the measurement of humidity (830). When the computed gas constant value is determined, the altitude of the pressure sensor may be estimated using the computed gas constant value (840).

In one implementation of comparing measurements to threshold conditions (810), the ambient humidity level is compared to a maximum humidity above which an unacceptable error results when the altitude of a pressure sensor is estimated using a predefined gas constant for dry air instead of using a computed gas constant for the ambient non-dry air. If the ambient humidity exceeds the maximum humidity, then the altitude is estimated using the computed gas constant for the ambient non-dry air. If the ambient humidity does not exceed the maximum humidity, then the altitude is estimated using the predefined gas constant of dry air (or the computed gas constant for the ambient air if available).

In another implementation of comparing measurements to threshold conditions (810), the ambient temperature is used to identify a maximum humidity above which an unacceptable error results when the altitude of a pressure sensor is estimated using the predefined gas constant of dry air instead of using the computed gas constant for the ambient non-dry air, and the ambient humidity is compared to the maximum humidity for the ambient temperature. If the ambient humidity exceeds the maximum humidity, then the altitude is estimated using the computed gas constant for the ambient non-dry air. If the ambient humidity does not exceed the maximum humidity, then the altitude is estimated using the predefined gas constant of dry air (or the computed gas constant for the ambient air if available).

In yet another implementation of comparing measurements to threshold conditions (810), the ambient humidity is used to identify a maximum temperature above which an unacceptable error results when the altitude of a pressure sensor is estimated using the predefined gas constant of dry air instead of using the computed gas constant for the ambient non-dry air, and the ambient temperature is compared to the maximum temperature for the ambient humidity. If the ambient temperature exceeds the maximum temperature, then the altitude is estimated using the computed gas constant for the ambient non-dry air. If the ambient temperature does not exceed the maximum temperature, then the altitude is estimated using the predefined gas constant of dry air (or the computed gas constant for the ambient air if available).

It is to be understood that various threshold conditions could be set so that not meeting a threshold condition results in using the measurement of humidity to estimate the altitude, while meeting the threshold condition results in not using the measurement of humidity to estimate the altitude. For example, if a measurement of humidity is not below some threshold humidity level, the measurement of humidity is used to estimate the altitude; and, if the measurement of humidity is below some threshold humidity level, the measurement of humidity is not used to estimate the altitude.

Although described in terms of humidity, this discussion broadly applies to any situation where the composition of the air in an environment is different from standard air composition, resulting in a local change in mass density of the atmosphere. Besides humidity, this would include pollutants, a depleted oxygen environment, or excess carbon dioxide, among other atmospheric conditions that include non-standard atmospheric compositions. The approaches described herein also apply in confined spaces where significant amounts of other gases might be trapped, such as inside a chemical storage tank, in a cave, or in a structure filled with smoke and other combustion gases.

Attention is now turned to different ways of estimating relative altitude using pressure and temperature.

Additional Approaches for Estimating Relative Altitude

As previously indicated, a pressure measurement from a pressure sensor may be used to estimate the altitude of the pressure sensor. In order to translate pressure measurements into an estimate of the altitude of the pressure sensor, a number of additional pieces of information are often required. One formula for relating pressure to altitude may be used. This formula is based upon the weight of a column of air, as follows:

$$z_1 - z_2 = -\frac{RT}{g} \ln\left(\frac{P_1}{P_2}\right)$$

where $z_1$ and $z_2$ are two altitudes, and $P_1$ and $P_2$ are the corresponding pressures at those altitudes, and T is the temperature of the air (in K) (e.g., an outside temperature of an environment when reference sensors are outside, or an indoor temperature in a climate-controlled environment when reference sensors are inside the climate-controlled environment), $R=287.052$ m$^2$/Ks$^2$ is the gas constant and $g=9.80665$ m/s$^2$ is the acceleration due to gravity. Note that this formula provides relative information, determining the difference in altitude for a difference in pressure. This formula is generally used with $z_2=0$, so that $P_2$ is the sea level pressure. Because sea level air pressure varies significantly with weather conditions and with location, the sea level pressure is needed in addition to the temperature and pressure at the site where altitude is to be determined. When applying standard atmosphere conditions, with T=15 C and P=101,325 Pa, it is found that a 1 m increase in altitude corresponds to a 12.01 Pa decrease in pressure.

To determine altitude with a resolution of 1 floor (about 3 meters), sea level pressure must be known with accuracy significantly finer than 36 Pa. It is also worth noting that because T is measured in Kelvin, a 3° C. (or K) error in temperature will correspond to approximately a 1% error in altitude. This can become significant when determining altitude significantly above sea level, and when trying to resolve upper floors in a high rise building. Thus, for determining altitude with a resolution of 1 m, sensors with high accuracy and resolution are needed. In order to fit in a mobile device, these sensors should be low cost, low power and small size. Note that commercial weather grade sensors do not provide this level of accuracy or resolution.

In order to estimate altitude to 1 m accuracy, a reference sensor system for providing reference pressure information may be used. The reference sensor system should be able to provide measurements that are close in temperature, distance and time to the unknown location. Some systems include the following elements: a mobile sensor that determines pressure and possibly temperature and humidity at the unknown location with sufficient accuracy; an array of reference sensors that determine pressure, temperature and humidity at known locations with sufficient accuracy; an estimation algorithm that inputs all reference sensor data, reference sensor locations and other augmenting information to generate an accurate reference pressure estimation at a location of interest; and a communications link between the reference sensors and the mobile sensors. In some embodiments, the reference sensors are located near a transmitter that broadcast positioning signals that carry ranging and positioning system information.

A description of a formulation to compute a reference level altitude is described below. Given reference pressure sensors at n transmitters, a sea level pressure is estimated based on the reference sensor outputs. This can be accomplished in two steps, but is not so limited. At a first step, given each reference sensor altitude $h_i$ (in meters) above a sea level at transmitter i, and the pressure $p_i$ (in Pascal) and the temperature $T_i$ (in Kelvin) readings from the reference sensor, the sea level atmospheric pressure $P_i$ is calculated at a location with latitude $x_i$ and longitude $y_i$ (in degrees), using the formula below:

$$P_i = p_i e^{\frac{gh_i}{RT_i}},$$

where g is the gravitational acceleration constant and R is the specific gas constant for air. At a second step, after calculating the sea level pressures at all n transmitter locations, and obtaining the latitude $x_0$ and longitude $y_0$ information of the mobile device, the equivalent sea level pressure is estimated at the mobile device location $P_0$ with the formula below:

$$P_0 = \sum_{i=1}^{n} W_i P_i$$

where $W_i=W_i(x_0, y_0, x_i, y_i)$ is the weighting function depending on both the mobile device location and the reference site i location. The following information may be used to estimate the altitude of the mobile device: reference sensor location (latitude and longitude) with one meter accuracy; altitude of reference sensor with at least 0.1-0.2 m accuracy; measured temperature of air at reference sensor location (which may be filtered or averaged); measured pressure of air at reference sensor location (which may be filtered, sensor temperature compensation, and any other local calibration such as offset); and a measure of confidence. Additional details are provided below.

One process for determining altitude from pressure readings involves converting the measurements at a reference location to the equivalent sea level pressure, and then using that to determine the altitude of the unknown pressure sensor. The standard formula is:

$$z = -\frac{RT}{g}\ln\left(\frac{P}{P_0}\right)$$

Note that a minus sign is present, since altitude may be measured as positive moving away from the surface of the earth. This formula relates, z, the altitude above a sea level, to the atmospheric temperature (T) and pressure (P) at that point, and air pressure ($P_0$) at sea level.

One additional problem with applying this formula is that the altitude is directly proportional to the temperature, a measured quantity not known precisely. This means that a 1% error in temperature will result in a 1% error in altitude. When used near sea level this will not be a significant problem. However, when this formula is applied in tall buildings and especially in higher altitude areas, such as Denver, a 1% error in altitude may be significant when attempting to resolve floor level altitude. For example, the altitude of Denver is about 1608 m. Thus, a 1% error in temperature will result in an error in altitude above sea level of 16 m in Denver. This is nearly 5 floors.

One way to avoid this sensitivity to temperature accuracy is to recognize that the formula above is actually a relative formula. That is the formula can be generalized to:

$$z_1 - z_2 = -\frac{RT}{g}\ln\left(\frac{P_1}{P_2}\right)$$

where $z_1$ and $z_2$ are any two altitudes, and $P_1$ and $P_2$ are the pressures at those altitudes. It is only a matter of convention that $z_2$ was set to 0, and thus $P_2$ becomes the sea level pressure, which is often above sea level.

Instead of using sea level as the reference point, any convenient altitude could be used. For example, the mean altitude of the city would be reasonable, or the mean altitude of the reference sensors used for collecting pressure data would work. As long as a reference altitude is selected to keep the altitude differences small, the impact of temperature error will not be significant. However, all devices involved in the system need to know the reference altitude.

Other Aspects

Functionality and operation disclosed herein may be embodied as one or more methods implemented, in whole or in part, by machine(s)—e.g., processor(s), computers, or other suitable means known in the art—at one or more locations, which enhances the functionality of those machines, as well as computing devices that incorporate those machines. Non-transitory machine-readable media embodying program instructions adapted to be executed to implement the method(s) are also contemplated. Execution of the program instructions by one or more processors cause the processors to carry out the method(s).

It is noted that method steps described herein may be order independent, and can therefore be performed in an order different from that described. It is also noted that different method steps described herein can be combined to form any number of methods, as would be understood by one of skill in the art. It is further noted that any two or more steps described herein may be performed at the same time.

By way of example, not by way of limitation, method(s) and processor(s) or other means may: compute an estimated altitude of the first pressure sensor using a first measurement of pressure from the first pressure sensor at the first location, a second measurement of pressure from a second pressure sensor at a second location, an altitude of the second pressure sensor, a measurement of temperature from a temperature sensor at the second location or a third location, and a measurement of humidity from a humidity sensor.

Method(s) and processor(s) or other means may further or alternatively: determine whether the measurement of humidity meets a threshold humidity condition; estimate the estimated altitude of the first pressure sensor using a computed gas constant value that is based on the measurement of humidity when the measurement of humidity meets the threshold humidity condition; and estimate the estimated altitude of the first pressure sensor using a predefined gas constant value for dry air that is not based on the measurement of humidity when the measurement of humidity does not meet the threshold humidity condition.

In accordance with some aspects, the measurement of humidity meets the threshold humidity condition when the measurement of humidity exceeds a predefined humidity value.

Method(s) and processor(s) or other means may further or alternatively: use the measurement of temperature to identify the predefined humidity value.

Method(s) and processor(s) or other means may further or alternatively: determine whether the measurement of temperature meets a threshold temperature condition; estimate the estimated altitude of the first pressure sensor using a computed gas constant value that is based on the measurement of humidity when the measurement of temperature meets the threshold temperature condition; and estimate the estimated altitude of the first pressure sensor using a predefined gas constant value for dry air that is not based on the measurement of humidity when the measurement of temperature does not meet the threshold temperature condition.

In accordance with some aspects, the measurement of temperature meets the threshold temperature condition when the measurement of temperature exceeds a predefined temperature value.

Method(s) and processor(s) or other means may further or alternatively: use the measurement of humidity to identify the predefined temperature value.

Method(s) and processor(s) or other means may further or alternatively: estimate the estimated altitude of the first pressure sensor using a predefined gas constant value for dry air that is not based on the measurement of humidity; determine an adjustment for the estimated altitude using the measurement of humidity; and adjust the estimated altitude using the adjustment.

In accordance with some aspects, the first pressure sensor is coupled to a mobile device that is located at a first location during a first time period, and a second location during a second time period, wherein the humidity sensor, the temperature sensor and the second pressure sensor are located within 6 meters of each other.

In accordance with some aspects, the computed air density value is further based on a measurement of other gas mixtures in the air.

In accordance with some aspects, the computed air density value is further based on a water vapor saturation pressure.

The illustrative methods described herein may be implemented, performed, or otherwise controlled by suitable hardware known or later-developed by one of ordinary skill in the art, or by firmware or software executed by processor(s), or any combination of hardware, software and firmware. Software may be downloadable and non-downloadable at a particular system. Such software comprises a machine-implemented component that, once loaded on a machine like a processor or a computer, changes the operation of that machine.

Systems on which methods described herein are performed may include one or more means that implement those methods. For example, such means may include processor(s) or other hardware that, when executing instructions (e.g., embodied in software or firmware), perform any method step disclosed herein. For example, methods may be carried out by a processor of the mobile device, where the processor processes measurements made by one or more sensors of the mobile device and/or received by a receiver of the mobile device from sensors at a reference location. Similarly, methods may be carried out by a processor that is not co-located with the mobile device. A processor may include, or be included within, a computer or computing device, a controller, an integrated circuit, a "chip", a system on a chip, a server, other programmable logic devices, other circuitry, or any combination thereof.

A mobile device may be in the form of a computing device (e.g., a cellular or smart phone, a tablet device, a PDA, a notebook, a digital camera, an asset tracking tag, a wearable device such as an ankle bracelet or other computing device). A mobile device may also take the form of any component of the mobile device system described above.

"Memory" may be accessible by a machine (e.g., a processor), such that the machine can read/write information from/to the memory. Memory may be integral with or separate from the machine. Memory may include a non-transitory machine-readable medium having machine-readable program code (e.g., instructions) embodied therein that is adapted to be executed to implement each of the methods and method steps disclosed herein. Memory may include any available storage media, including removable, non-removable, volatile, and non-volatile media—e.g., integrated circuit media, magnetic storage media, optical storage media, or any other computer data storage media. As used herein, machine-readable media includes all forms of machine-readable media except to the extent that such media is deemed to be non-statutory (e.g., transitory propagating signals).

Application programs may carry out aspects by receiving, converting, processing, storing, retrieving, transferring and/or exporting data, which may be stored in a hierarchical, network, relational, non-relational, object-oriented, or other data source. A data source may be a single storage device or realized by multiple (e.g., distributed) storage devices.

All of the information disclosed herein may be represented by data, and that data may be transmitted over any communication pathway using any protocol, stored on a data source, and processed by a processor. For example, transmission of data may be carried out using a variety of wires, cables, radio signals and infrared light beams, and an even greater variety of connectors, plugs and protocols even if not shown or explicitly described. Systems/platforms described herein may exchange information with each other (and with other systems that are not described) using any known or later-developed communication technology, including WiFi, Bluetooth, NFC and other communication network technologies. Carrier waves may be used to transfer data and instructions through electronic, optical, air, electromagnetic, radio frequency, or other signaling media over a network using network transfer protocols, including data that is transferred in data signals. Data, instructions, commands, information, signals, bits, symbols, and chips disclosed herein may be represented by voltages, currents, electromagnetic waves, magnetic fields or particles, optical fields or particles, or any combination thereof.

Different systems disclosed herein may be geographically dispersed from one another in different regions (e.g., cities, countries), such that different method steps are performed in different regions and by different systems. An output from one system may cause another system to perform a method even if intervening steps occur between the output and performance of the method.

Features in system figures that are illustrated as rectangles may refer to hardware, firmware or software, each of which may comprise a component of a device. It is noted that lines linking two such features may be illustrative of data transfer between those features. Such transfer may occur directly between those features or through intermediate features even if not illustrated. Where no line connects two features, transfer of data between those features is contemplated unless otherwise stated. Thus, such lines are provided to illustrate certain aspects, but should not be interpreted as limiting. The words comprise, comprising, include, including and the like are to be construed in an inclusive sense (i.e., not limited to) as opposed to an exclusive sense (i.e., consisting only of). Words using the singular or plural number also include the plural or singular number, respectively. The words or and, as used in the Detailed Description, cover any of the items and all of the items in a list. The words some, any and at least one refer to one or more. The term may is used herein to indicate an example, not a requirement—e.g., an object that may perform an operation or may have a characteristic need not perform that operation or have that characteristic in each embodiment, but that object performs that operation or has that characteristic in at least one embodiment. This disclosure is not intended to be limited to the aspects shown herein but is to be accorded the widest scope understood by a skilled artisan, including equivalents.

RELATED APPLICATIONS

This application relates to U.S. Patent Application Ser. No. 61/939,814 (Feb. 14, 2014), entitled IMPROVED ACCURACY IN DETERMINING ELEVATION FROM PRESSURE, the content of which is hereby incorporated by reference herein in its entirety.

The invention claimed is:

1. A method for estimating an altitude of a first pressure sensor at a first location, the method comprising:

determining whether a measurement of humidity from a humidity sensor meets a threshold humidity condition or whether a measurement of temperature from a temperature sensor meets a threshold temperature condition; and computing an estimate of the altitude of the first pressure sensor using a first measurement of pressure from the first pressure sensor at the first location, a second measurement of pressure from a second pressure sensor at a second location, an altitude of the second pressure sensor, the measurement of temperature from the temperature sensor, and either (1) a computed gas constant value that is based on the measurement of humidity from the humidity sensor, or (2) a predefined gas constant value that is not based on the measurement of humidity, wherein the estimate of the altitude of the first pressure sensor is computed using (1) the computed gas constant value when the measurement of humidity meets the threshold humidity condition or when the measurement of temperature meets the threshold temperature condition, or (2) the predefined gas constant value when the measurement of humidity does not meet the threshold humidity condition or when the measurement of temperature does not meet the threshold temperature condition.

2. The method of claim 1, wherein the method comprises:
determining whether the measurement of humidity meets the threshold humidity condition;
computing, when the measurement of humidity meets the threshold humidity condition, the estimate of the altitude of the first pressure sensor using the computed gas constant value that is based on the measurement of humidity; and
computing, when the measurement of humidity does not meet the threshold humidity condition, the estimate of the altitude of the first pressure sensor using the predefined gas constant value that is not based on the measurement of humidity.

3. The method of claim 2, wherein the measurement of humidity meets the threshold humidity condition when the measurement of humidity exceeds a predefined humidity value.

4. The method of claim 3, wherein the method comprises: using the measurement of temperature to identify the predefined humidity value.

5. The method of claim 1, wherein the method comprises:
determining whether the measurement of temperature meets a threshold temperature condition;
computing, when the measurement of temperature meets the threshold temperature condition, the estimate of the altitude of the first pressure sensor using the computed gas constant value that is based on the measurement of humidity; and
computing, when the measurement of temperature does not meet the threshold temperature condition, the estimate of the altitude of the first pressure sensor using the predefined gas constant value that is not based on the measurement of humidity.

6. The method of claim 5, wherein the measurement of temperature meets the threshold temperature condition when the measurement of temperature exceeds a predefined temperature value.

7. The method of claim 6, wherein the method comprises: using the measurement of humidity to identify the predefined temperature value.

8. The method of claim 1, wherein the method comprises:
computing the estimate of the altitude of the first pressure sensor using the predefined gas constant value that is not based on the measurement of humidity;
determining an adjustment for the estimate of the altitude using the measurement of humidity; and
adjusting the estimate of the altitude using the adjustment.

9. The method of claim 1, wherein the humidity sensor, the temperature sensor and the second pressure sensor are located within 6 meters of each other.

10. The method of claim 1, wherein the method comprises:
computing the estimate of the altitude of the first pressure sensor using the computed gas constant value that is based on the measurement of humidity.

11. The method of claim 2, wherein the method comprises:
computing the estimate of the altitude of the first pressure sensor using the computed gas constant value that is based on the measurement of humidity.

12. The method of claim 5, wherein the method comprises:
computing the estimate of the altitude of the first pressure sensor using the computed gas constant value that is based on the measurement of humidity.

13. The method of claim 1, wherein the predefined gas constant value is a gas constant value for dry air, and the computed gas constant value is computed by applying a multiplier to the gas constant value for dry air.

14. The method of claim 1, wherein the computed gas constant value is computed as being equal to $R\_da*(1+1.609*x)/(1+x)$, where $R\_da$ is a gas constant value for dry air, and x is a humidity ratio.

15. The method of claim 14, wherein the humidity ratio x is equal to $0.62198*\phi*p\_ws/(p\_a-\phi*p\_ws)$, where $p\_ws$ is a water vapor saturation pressure, $p\_a$ is a measured air pressure, and $\phi$ is the measurement of humidity.

16. The method of claim 1, wherein one or more processors compute the estimate of the altitude using the following mathematical relationships: $(R*T/g)*\ln(P\_2/P\_1)$, where $P\_2$ is the second measurement of pressure or a sea-level pressure calculated using both the second measurement of pressure and the altitude of the second pressure sensor, $P\_1$ is the first measurement of pressure, T is the measurement of temperature, g is acceleration due to gravity, and R is either the computed gas constant value or the predefined gas constant value.

17. One or more non-transitory processor-readable media embodying program instructions that, when executed by one or more processors, cause the one or more processors to implement a method for estimating an altitude of a first pressure sensor at a first location, the method comprising:
determining whether a measurement of humidity from a humidity sensor meets a threshold humidity condition or whether a measurement of temperature from a temperature sensor meets a threshold temperature condition; and
computing an estimate of the altitude of the first pressure sensor using a first measurement of pressure from the first pressure sensor at the first location, a second measurement of pressure from a second pressure sensor at a second location, an altitude of the second pressure sensor, the measurement of temperature from the temperature sensor, and either (1) a computed gas constant value that is based on the measurement of humidity from the humidity sensor, or (2) a predefined gas constant value that is not based on the measurement of humidity, wherein the estimate of the altitude of the first pressure sensor is computed using (1) the computed gas constant value when the measurement of humidity meets the threshold humidity condition or when the measurement of temperature meets the threshold temperature condition, or (2) the predefined gas constant value when the measurement of humidity does not meet the threshold humidity condition or when the measurement of temperature does not meet the threshold temperature condition.

18. The one or more non-transitory processor-readable media of claim 17, wherein the method comprises:
determining whether the measurement of humidity meets the threshold humidity condition;
computing, when the measurement of humidity meets the threshold humidity condition, the estimate of the altitude of the first pressure sensor using the computed gas constant value that is based on the measurement of humidity; and
computing, when the measurement of humidity does not meet the threshold humidity condition, the estimate of the altitude of the first pressure sensor using the predefined gas constant value that is not based on the measurement of humidity.

19. The one or more non-transitory processor-readable media of claim 18, wherein the measurement of humidity meets the threshold humidity condition when the measurement of humidity exceeds a predefined humidity value.

20. The one or more non-transitory processor-readable media of claim 19, wherein the method comprises:
using the measurement of temperature to identify the predefined humidity value.

21. The one or more non-transitory processor-readable media of claim 17, wherein the method comprises:
determining whether the measurement of temperature meets a threshold temperature condition;
computing, when the measurement of temperature meets the threshold temperature condition, the estimate of the altitude of the first pressure sensor using the computed gas constant value that is based on the measurement of humidity; and
computing, when the measurement of temperature does not meet the threshold temperature condition, the estimate of the altitude of the first pressure sensor using the predefined gas constant value that is not based on the measurement of humidity.

22. The one or more non-transitory processor-readable media of claim 21, wherein the measurement of temperature meets the threshold temperature condition when the measurement of temperature exceeds a predefined temperature value.

23. The one or more non-transitory processor-readable media of claim 22, wherein the method comprises:
using the measurement of humidity to identify the predefined temperature value.

24. The one or more non-transitory processor-readable media of claim 17, wherein the method comprises:
computing the estimate of the altitude of the first pressure sensor using the predefined gas constant value that is not based on the measurement of humidity;
determining an adjustment for the estimate of the altitude using the measurement of humidity; and
adjusting the estimate of the altitude using the adjustment.

25. The one or more non-transitory processor-readable media of claim 17, wherein the humidity sensor, the temperature sensor and the second pressure sensor are located within 6 meters of each other.

26. The one or more non-transitory processor-readable media of claim 17, wherein the method comprises:
computing the estimate of the altitude of the first pressure sensor using the computed gas constant value that is based on the measurement of humidity.

27. The one or more non-transitory processor-readable media of claim 18, wherein the method comprises:
computing the estimate of the altitude of the first pressure sensor using the computed gas constant value that is based on the measurement of humidity.

28. The one or more non-transitory processor-readable media of claim 21, wherein the method comprises:
computing the estimate of the altitude of the first pressure sensor using the computed gas constant value that is based on the measurement of humidity.

29. The one or more non-transitory processor-readable media of claim 17, wherein the predefined gas constant value is a gas constant value for dry air, and the computed gas constant value is computed by applying a multiplier to the gas constant value for dry air.

30. The one or more non-transitory processor-readable media of claim 17, wherein the computed gas constant value is computed as being equal to $R\_da*(1+1.609*x)/(1+x)$, where $R\_da$ is a gas constant value for dry air, and x is a humidity ratio.

31. The one or more non-transitory processor-readable media of claim 30, wherein the humidity ratio x is equal to $0.62198*\phi*p\_ws/(p\_a-\phi*p\_ws)$, where $p\_ws$ is a water vapor saturation pressure, $p\_a$ is a measured air pressure, and $\phi$ is the measurement of humidity.

32. The one or more non-transitory processor-readable media of claim 20, wherein the estimate of the altitude is computed using the following mathematical relationships: $(R*T/g) * \ln(P\_2/P\_1)$, where $P\_2$ is the second measurement of pressure or a sea-level pressure calculated using both the second measurement of pressure and the altitude of the second pressure sensor, $P\_1$ is the first measurement of pressure, T is the measurement of temperature, g is acceleration due to gravity, and R is either the computed gas constant value or the predefined gas constant value.

33. A system for estimating an altitude of a first pressure sensor at a first location, wherein the system comprises one or more processors and one or more non-transitory processor-readable media storing instructions that are operable, when executed by the one or more processors, to cause the one or more processors to perform operations comprising:
determining whether a measurement of humidity from a humidity sensor meets a threshold humidity condition or whether a measurement of temperature from a temperature sensor meets a threshold temperature condition; and
computing an estimate of the altitude of the first pressure sensor using a first measurement of pressure from the first pressure sensor at the first location, a second measurement of pressure from a second pressure sensor at a second location, an altitude of the second pressure sensor, the measurement of temperature from the temperature sensor, and either (1) a computed gas constant value that is based on the measurement of humidity from the humidity sensor, or (2) a predefined gas constant value that is not based on the measurement of humidity,
wherein the estimate of the altitude of the first pressure sensor is computed using (1) the computed gas constant value when the measurement of humidity meets the threshold humidity condition or when the measurement of temperature meets the threshold temperature condition, or (2) the predefined gas constant value when the measurement of humidity does not meet the threshold humidity condition or when the measurement of temperature does not meet the threshold temperature condition.

* * * * *